(12) United States Patent
Gralla et al.

(10) Patent No.: US 8,779,169 B2
(45) Date of Patent: Jul. 15, 2014

(54) PROCESS FOR THE PREPARATION OF 2 SUBSTITUTED TETRAHYDROPYRANOLS

(75) Inventors: Gabriele Gralla, Mannheim (DE); Ralf Pelzer, Fürstenberg (DE)

(73) Assignee: BASF SE, Ludwigshafen (DE)

( * ) Notice: Subject to any disclaimer, the term of this patent is extended or adjusted under 35 U.S.C. 154(b) by 142 days.

(21) Appl. No.: 13/116,546

(22) Filed: May 26, 2011

(65) Prior Publication Data

US 2011/0295024 A1 Dec. 1, 2011

Related U.S. Application Data

(60) Provisional application No. 61/348,756, filed on May 27, 2010.

(51) Int. Cl.
*C07D 309/10* (2006.01)

(52) U.S. Cl.
CPC ..................... *C07D 309/10* (2013.01)
USPC ......................................... 549/423

(58) Field of Classification Search
CPC ..................................... C07D 309/10
USPC ......................................... 549/423
See application file for complete search history.

(56) References Cited

U.S. PATENT DOCUMENTS

| 2,271,134 | A | 1/1942 | Will et al. |
| 4,230,533 | A | 10/1980 | Giroux |
| 5,530,127 | A | 6/1996 | Reif et al. |
| 6,262,317 | B1 | 7/2001 | Becker et al. |
| 2011/0295024 | A1 | 12/2011 | Gralla et al. |
| 2011/0306779 | A1 | 12/2011 | Gralla et al. |
| 2012/0059177 | A1 | 3/2012 | Gralla et al. |

FOREIGN PATENT DOCUMENTS

| CN | 1222902 A | 7/1999 |
| DE | 10223971 A1 | 12/2003 |
| EP | 122 367 A2 | 10/1984 |
| EP | 126 288 A2 | 11/1984 |
| EP | 133 510 A1 | 2/1985 |
| EP | 640 367 A1 | 3/1995 |
| EP | 0696572 A1 | 2/1996 |
| EP | 1493737 A1 | 1/2005 |
| EP | 1516879 A1 | 3/2005 |
| JP | 2007-154069 A | * 6/2007 |
| JP | 2007154069 A | 6/2007 |
| SU | 825528 A1 | * 4/1981 |
| WO | WO-2010133473 A1 | 11/2010 |

OTHER PUBLICATIONS

Kawanobe et al, Machine translation of Detailed Description Section, JP 2007-154069 A, (2005).*
DeSilva, "Essentials of Ion Exchange", Presented at the 25th Annual WQA Conference, Mar. 17, 1999 (from Internet).*
Gevorkyan et al, Chemistry of Heterocyclic Compounds, No. 12, p. 1240-1242 (1982).*
Pankaj Gupta, Helvetica Chimica Acta, vol. 90, 2007, pp. 196-204.
Alexandra Macedo, J. Braz. Chem. Soc., vol. 21, 2010, pp. 1563-1571.
International Search Report PCT/EP2010/056403, (2010).
Thetrahedron Letters No. 51, pp. 4507-4508, 1970.
Definition of Ion Exchange Resins, from The Great Soviet Encyclopedia (1979) (from the Internet).
Ennenbach et al., www.digitalrefining.com/article/1000630 (Oct. 1980).
Ibatullin, Chemistry of Heterocyclic Compounds, vol. 25, 1989, pp. 1107-1109.
Thomson Scientific, London, 2007-564955.
Thomson Scientific, London, 1982-11549E.

* cited by examiner

*Primary Examiner* — Noble Jarrell
*Assistant Examiner* — Valerie Rodriguez-Garcia
(74) *Attorney, Agent, or Firm* — Drinker Biddle & Reath LLP

(57) ABSTRACT

The present invention relates to a process for the preparation of 2-substituted 4-hydroxy-4-methyltetrahydropyrans by reacting 3-methylbut-3-en-1-ol(isoprenol) with the corresponding alkenealdehydes in the presence of a strongly acidic ion exchanger with subsequent hydrogenation. Specifically, the present invention relates to a corresponding process for the preparation of 2-isobutyl-4-hydroxy-4-methyltetrahydropyran by reacting isoprenol with prenal, with subsequent hydrogenation.

18 Claims, No Drawings

PROCESS FOR THE PREPARATION OF 2 SUBSTITUTED TETRAHYDROPYRANOLS

CROSS-REFERENCE TO RELATED APPLICATIONS

This Application claims the benefit of U.S. Provisional Application 61/348,756 filed on May 27, 2010 which is incorporated by reference.

BACKGROUND OF THE INVENTION

The present invention relates to a process for the preparation of 2-substituted 4-hydroxy-4-methyltetrahydropyrans by reacting 3-methylbut-3-en-1-ol(isoprenol) with the corresponding alkenealdehydes in the presence of a strongly acidic ion exchanger with subsequent hydrogenation. Specifically, the present invention relates to a corresponding process for the preparation of 2-isobutyl-4-hydroxy-4-methyltetrahydropyran by reacting isoprenol with prenal, with subsequent hydrogenation.

Tetrahedron Letters No. 51, pages 4507-4508, 1970 describes the reaction of 3-alken-1-ols with aldehydes and their use for producing the aroma chemicals rose oxide and dihydrorose oxide. Also mentioned here is the reaction of 3-methylbutanal with isoprenol under acidic conditions.

SU 825 528 discloses a process for the preparation of di- and tetrahydropyrans and tetrahydropyranols by reacting 2-methylbuten-1-ol-4(isoprenol) with aldehydes or ketones in the presence of an acidic catalyst, where the acidic catalyst is used in an amount of from 0.0001 to 0.01% by weight, based on the amount of isoprenol, and the reaction is carried out at a temperature of from 0 to 25° C. in an organic solvent. The catalysts specified are the ion exchange resin KU-2 (sulfonated polystyrene resin), para-toluene sulfonic acid, sulfuric acid or perchloric acid. By way of example, the reaction of isoprenol with isobutyraldehyde in the presence of KU-2, inter alia, is described.

EP 1 493 737 A1 discloses a process for the preparation of mixtures of ethylenically unsaturated 4-methyl- and 4-methylenepyrans and the corresponding hydroxypyrans by reacting the corresponding aldehydes with isoprenol, where the reaction is initiated in a reaction system in which the molar ratio of aldehyde to isoprenol is greater than 1, i.e. the aldehyde is used in excess. Moreover, the document discloses the subsequent dehydrogenation of said mixtures to give the desired ethylenically unsaturated pyrans. Suitable catalysts specified for the first reaction step are mineral acids, such as hydrochloric acid or sulfuric acid, but preferably methanesulfonic acid or para-toluene sulfonic acid.

JP 2007-154069 relates to 2-substituted 4-hydroxytetrahydropyrans with a content of the cis-diastereomer of from 70 to 95% by weight. Moreover, the document discloses a process for the preparation of same, by reacting isoprenol with a corresponding aldehyde in the presence of an aqueous solution of an acidic catalyst. Here, the reaction has to be carried out at a concentration of the aqueous catalyst solution either in the range from 1:10% by weight at a temperature of from 0 to 100° C., or in the region of 10% by weight or above at a temperature of from 0 to 30° C. The possible acidic catalysts mentioned are generally also ion exchange resins.

BRIEF SUMMARY OF THE INVENTION

Starting from this prior art, the object of the present invention was to provide a process for the preparation of 2-substituted 4-hydroxy-4-methyltetrahydropyrans, in particular of 2-isobutyl-4-hydroxy-4-methyltetrahydropropan(=pyranol), which can be carried out in a manner which is easy to handle in terms of processing and with high overall yield for the highest possible chemoselectivity on an industrial scale. In the process, it should be possible to use inexpensive, easy-to-recover and readily reusable starting compounds and reagents and/or catalysts.

Surprisingly, the object was achieved according to the invention through the provision of a process for the preparation of 2-substituted 4-hydroxy-4-methyltetrahydropyrans of the formula (I)

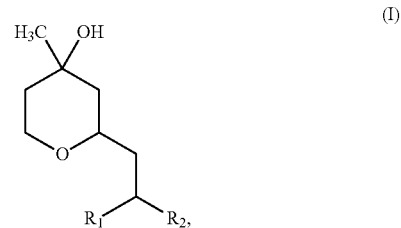

where the radical $R_1$ is a straight-chain or branched alkyl radical having 1 to 5 carbon atoms, $R_2$ is hydrogen or a straight-chain or branched alkyl radical having 1 to 3 carbon atoms, comprising the reaction of 3-methylbut-3-en-1-ol of the formula (II)

with an aldehyde of the formula (III)

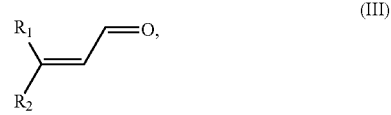

where the radicals $R_1$ and $R_2$, independently of one another, have the same meanings as given in formula (I), in the presence of water and in the presence of a strongly acidic cation exchanger to form the compound of the formula (IV)

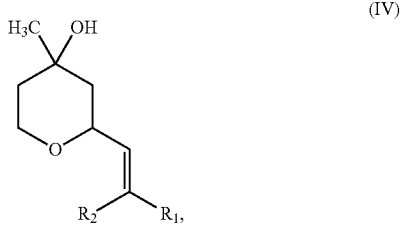

and hydrogenation of the compound of the formula (IV) in the presence of a catalyst to give a compound of the formula (I).

DETAILED DESCRIPTION OF THE INVENTION

Suitable starting materials for carrying out the process according to the invention are 3-methylbut-3-en-1-ol(isoprenol) of the formula (II),

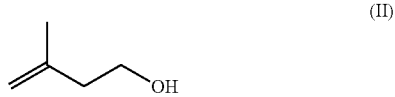

which is readily accessible by known processes from isobutene and formaldehyde on any scale and is commercially readily available. No particular requirements are placed on the purity, quality or preparation process of the isoprenol to be used according to the invention. It can be used as starting material in the course of the process according to the invention in standard commercial quality and purity with good success. Preference is given to using isoprenol which has a purity of 90% by weight or above, particularly preferably one with a purity of from 95 to 100% by weight and very particularly preferably one with a purity of from 97 to 99.9% by weight or even more preferably 98 to 99.8% by weight.

A further suitable starting material for carrying out the process according to the invention is an alkenealdehyde of the formula (III)

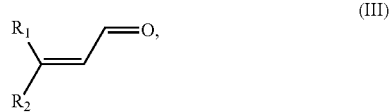

where the radical $R_1$ may be a straight-chain or branched alkyl radical having 1 to 5 carbon atoms and $R_2$ may be hydrogen or a straight-chain or branched alkyl radical having 1 to 3 carbon atoms.

An alkyl substituent $R_1$ is to be understood as meaning one which has 1 to 5 carbon atoms, such as, for example, methyl, ethyl, n-propyl, isopropyl, n-butyl, sec-butyl, tert-butyl or n-pentyl, preferably methyl, ethyl, n-propyl, isopropyl, and very particularly preferably methyl.

An alkyl substituent $R_2$ is to be understood as meaning one which has 1 to 3 carbon atoms, such as, for example, methyl, ethyl, n-propyl or isopropyl, preferably methyl or ethyl, and very particularly preferably methyl.

In the process according to the invention, the words "strongly acidic cation exchanger" mean that the ion exchanger is present in $H^+$ form.

According to the invention, very particularly preferred alkenealdehydes of the formula (III) are those in which the radical $R_1$ is a straight-chain or branched alkyl radical having 1 to 3 carbon atoms and the radical $R_2$ is an alkyl radical having 1 to 2 carbon atoms. According to the invention, preferred meanings for the radical $R_1$ are therefore, for example, methyl, ethyl, n-propyl and isopropyl, very particularly preferably methyl and preferred meanings for the radical $R_2$ are therefore methyl or ethyl and very particularly preferably methyl. As alkenealdehydes of the formula (III) accordingly to be used preferably according to the invention, the following may be mentioned: prenal(3-methyl-2-butenal), 2-butenal, 3-methyl-2-pentenal, 2-pentenal, 2-hexenal, 3-methyl-2-hexenal. An alkenealdehyde of the formula (III) to be used very particularly preferably according to the invention is prenal.

The starting materials isoprenol and the aldehyde of the formula (III) selected in each case to be used in the course of the process according to the invention can be reacted together in various quantitative ratios. Thus, it is possible to use one of the two starting materials in excess, in which case the level of the selected excess should vary within operationally and economically advantageous limits, but otherwise can in principle be freely chosen. Following the stoichiometry of the reaction according to the invention of isoprenol with the selected aldehyde of the formula (III), isoprenol and the aldehyde of the formula (III), preferably prenal, are used in a molar ratio in the range from 1:2 to 2:1, corresponding to a double molar excess of one of the starting materials. Within the context of a preferred embodiment, the process according to the invention is carried out in such a way that isoprenol and the aldehyde of the formula (III) are used in a molar ratio of from 0.7:1 to 2:1. The process according to the invention is particularly preferably carried out in such a way that isoprenol and the aldehyde of the formula (III) are used in a molar ratio of from 1:1 to 2:1. The process according to the invention is very particularly preferably carried out in such a way that isoprenol and the aldehyde of the formula (III) are used in a molar ratio of from 1:1 to 1.5:1.

The reaction of isoprenol with the selected aldehyde of the formula (III), preferably with prenal, that is to be carried out in the course of the process according to the invention for the preparation of the 2-substituted 4-hydroxy-4-methyltetrahydropyrans of the formula (I), preferably for the preparation of 2-isobutyl-4-hydroxy-4-methyltetrahydropyran, is carried out in the presence of water. This means that besides isoprenol, the aldehyde of the formula (III) and the selected strongly acidic cation exchanger, water is also added to the reaction mixture. In addition, the reaction mixture can also comprise small amounts of water which can be released by the dehydration of the desired process product of the formula (I) which possibly takes place as an undesired secondary reaction.

The reaction of the isoprenol with the selected aldehyde of the formula (III) is usually carried out in the presence of about at least 10 mol % of water, where the amount of water refers to the amount of the starting material isoprenol, optionally used in deficit, or to the aldehyde of the formula (III), or, in the case of the equimolar reaction of the two starting materials, to the quantitative amount of one of the two.

Above the stated value, the amount of water can be freely chosen and is limited only by processing or cost aspects, if at all, and can be used perfectly well in a large excess, for example in 10- to 100-fold excess or even more. Preferably, a mixture of isoprenol and the selected aldehyde of the formula (III), preferably prenal, is prepared with the selected amount of water such that the added water remains dissolved in the mixture of isoprenol and the selected aldehyde, i.e. no two-phase system is present.

Usually, in the course of the process according to the invention, the starting materials isoprenol and the selected aldehyde of the formula (III) are reacted in the presence of at least 25 mol %, preferably of at least 50 mol %, even more preferably of at least 75 and even more preferably of at least 90 to about 1000 mol %, of water, where the amount of water refers to the amount of the starting material isoprenol, optionally used in deficit, or to the aldehyde of the formula (III), or, in the case of the equimolar reaction of the two starting materials, to the quantitative amount of one of the two.

Within the context of a preferred embodiment, the reaction to be carried out according to the invention is carried out such that it is carried out in the presence of an at least equimolar amount of water, where the amount of water refers to the amount of the starting material isoprenol, optionally used in deficit, or to the aldehyde of the formula (III), or, in the case of the equimolar reaction of the two starting materials, to the quantitative amount of one of the two. Consequently, the reaction according to the invention of isoprenol with the selected aldehyde of the formula (III) is preferably carried out in the presence of from 100 to 250 mol %, particularly preferably 100 to 230 mol %, even more preferably 100 to 200 mol % and most preferably in the presence of from 100 to 180 mol %, of water, where the amount of water refers to the amount of the starting material isoprenol, optionally used in deficit, or to the aldehyde of the formula (III), or, in the case of the equimolar reaction of the two starting materials, to the quantitative amount of one of the two.

The specified starting materials, i.e. isoprenol and the aldehyde selected in each case and the water to be used in the above amount can be brought into contact with one another or be mixed in any desired order. Usually, a mixture of isoprenol and the selected aldehyde of the formula (III) is prepared with the selected amount of water and this mixture is used in the course of the reaction to be carried out according to the invention.

The reaction of isoprenol with the selected aldehyde of the formula (III) to be carried out in the course of the process according to the invention for preparing the desired 2-substituted 4-hydroxy-4-methyltetrahydropyrans of the formula (I), is carried out in the presence of a strongly acidic cation exchanger. Within the context of the present invention, the term strongly acidic cation exchanger is to be understood as meaning those cation exchangers which have strongly acidic groups, usually sulfonic acid groups, whose matrix may be gel-like or macroporous.

One preferred embodiment of the process according to the invention is accordingly one in which a strongly acidic cation exchanger comprising or having sulfonic acid groups is used.

Strongly acidic cation exchangers are in particular ion exchange resins in the H+ form. As such, the following are for example suitable:

strongly acidic ion exchangers (such as e.g. Amberlyst, Amberlite, Dowex, Lewatit, Purolite, Serdolit) which are based on polystyrene, and which comprise copolymers of styrene and divinylbenzene as carrier matrix with sulfonic acid groups in H+ form,
ion exchanger groups functionalized with sulfonic acid groups ($-SO_3H$).

The ion exchangers differ in the structure of their polymer backbones, and a distinction is made between gel-like and macroporous resins. The strongly acidic ion exchange resins are generally regenerated with hydrochloric acid and/or sulfuric acid.

Nafion® here is perfluorinated ion exchange materials consisting of fluorocarbon base chains and perfluorinated side chains which comprise sulfonic acid groups. The resins are prepared by a copolymerization of perfluorinated, terminally unsaturated and sulfonyl-fluoride-functionilized ethoxylates with perfluoroethene. Nafion® belongs to the gel-like ion exchange resins. One example of such a perfluorinated polymeric ion exchange resin which may be mentioned is Nafion® NR-50.

One particularly preferred embodiment of the process according to the invention is one in which at least one strongly acidic cation exchanger is used in the H+ form, where the ion exchanger comprises a polymer backbone having sulfonic acid groups and is either gel-like or comprises macroporous resins.

One very particularly preferred embodiment of the process according to the invention is one in which the ion exchanger is based on a polystyrene backbone with sulfonic acid groups or on a perfluorinated ion exchange resin with sulfonic acid groups.

The commercially available strongly acidic cation exchangers are known under the trade names Lewatit® (Lanxess), Purolite® (The Purolite Company), Dowex® (Dow Chemical Company), Amberlite® (Rohm and Haas Company), Amberlyst™ (Rohm and Haas Company).

Strongly acidic cation exchangers preferred according to the invention that may be mentioned are, for example: Lewatit® K 1221, Lewatit® K 1461, Lewatit® K 2431, Lewatit® K 2620, Lewatit® K 2621, Lewatit® K 2629, Lewatit® K 2649, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nafion® NR-50.

Within the scope of a preferred embodiment, the reaction of isoprenol with the selected aldehyde of the formula (III) to be carried out according to the invention is carried out in the presence of at least one strongly acidic cation exchanger which is selected from the group of the cation exchangers comprising Lewatit® K 1221, Lewatit® K 2629, Amberlyst™ 131, Puralite® SGC650, Purolite® C100H, Purolite® C150H, Amberlite® IR 120 and Dowex® 50X8.

Strongly acidic cation exchangers that are particularly preferred according to the invention are the cation exchangers Amberlyst™ 131 and/or Lewatit® K 1221.

A strongly acidic cation exchanger that is very particularly preferred according to the invention is Amberlyst™ 131, which, like the other specified cation exchangers, is commercially available.

To carry out the reaction according to the invention of isoprenol with the aldehyde of the formula (III), the specified starting materials and the selected amount of water, preferably in the form of a mixture, are brought into contact with the selected strongly acidic cation exchanger. The amount of cation exchanger to be used is not critical and can be freely chosen within wide limits taking into consideration the cost and processing aspect. The reaction can accordingly be carried out either in the presence of catalytic amounts or in the presence of large excesses of the selected strongly acidic cation exchanger. Usually, the selected cation exchanger is used in an amount of from about 5 to about 40% by weight, preferably in an amount of from about 20 to about 40% by weight and particularly preferably in an amount of from about 20 to about 30% by weight, in each case based on the sum of isoprenol used and aldehyde of the formula (III). Here, the data refer to the ready-to-use cation exchanger, which is usually pretreated with water and accordingly can comprise amounts of up to about 70% by weight, preferably from about 30 to about 65% by weight and particularly preferably from about 40 to about 65% by weight, of water. Particularly in the case of a discontinuous procedure, an addition of water beyond this may therefore be unnecessary when carrying out the process according to the invention.

The specified strongly acidic cation exchangers can be used either individually or in the form of mixtures with one another in the course of the process according to the invention.

The reaction to be carried out according to the invention can, if desired, also be carried out in the presence of a solvent that is inert under the reaction conditions, such as, for example, tert-butyl methyl ether, cyclohexane, toluene, hexane or xylene. The specified solvents can be used on their own or in the form of mixtures with one another. Within the context of a preferred embodiment of the process according to the invention, the reaction of isoprenol with the selected aldehyde of the formula (III) is carried out without addition of an organic solvent.

The reaction of isoprenol with the selected aldehyde of the formula (III) to be carried out according to the invention in the presence of water and in the presence of a strongly acidic cation exchanger is usually carried out at a temperature in the range from 0 to 100° C., preferably at a temperature in the range from 20 to 90° C. and particularly preferably at a temperature in the range from 20 to 80° C., where the temperature refers to that of the reaction mixture.

The reaction to be carried out according to the invention can, if desired, be carried out discontinuously or continuously. Here, for example in the discontinuous case, the reaction can be undertaken such that a mixture of isoprenol, the selected aldehyde of the formula (III) and water is initially introduced into a suitable reaction vessel and the strongly acidic cation exchanger is added. Following conclusion of the reaction, the cation exchanger can then be separated off from the resulting reaction mixture by suitable separation methods, preferably by filtration or by centrifugation. The order in which the individual reaction components are brought into contact is not critical and can be varied according to the particular processing embodiment.

Within the context of a preferred embodiment, the reaction of isoprenol with the selected aldehyde of the formula (III) to be carried out according to the invention is carried out continuously. For this, for example a mixture of the starting materials isoprenol and aldehyde of the formula (III) to be reacted can be prepared with water and this mixture can be continuously brought into contact with a strongly acidic cation exchanger. For this, the selected cation exchanger can be introduced, for example, into a suitable flow reactor, for example a stirred reactor with inlet and outlet or a tubular reactor, and the starting materials and the water can be discharged continuously into this and the reaction mixture can be continuously discharged. In this connection, the starting materials and the water can, if desired, be introduced into the flow reactor as individual components or else in the form of a mixture as described above.

The hydrogenation step of the process according to the invention is preferably carried out in the presence of hydrogen and in the presence of a heterogeneous catalyst, where the heterogeneous catalyst to be used comprises 30 to 70% by weight, preferably 40 to 60% by weight, of oxygen-containing compounds of nickel, calculated as NiO, 15 to 45% by weight, preferably 20 to 40% by weight, of oxygen-containing compounds of zirconium, calculated as $ZrO_2$, 5 to 30% by weight, preferably 10 to 25% by weight, of oxygen-containing compounds of copper, calculated as CuO, and 0.1 to 10% by weight, preferably 0.5 to 5% by weight, of oxygen-containing compounds of molybdenum, calculated as $MoO_3$, optionally alongside further components in an amount of from 0 to 10% by weight, preferably 0 to 5% by weight, such as, for example, graphite. Here, the data in % by weight refer to the dry, nonreduced catalyst.

Within the context of one preferred embodiment of the process according to the invention, for the procedure, use is made of those catalysts comprising 45 to 55% by weight of oxygen-containing compounds of nickel, calculated as NiO, 25 to 35% by weight of oxygen-containing compounds of zirconium, calculated as $ZrO_2$, 5 to 20% by weight of oxygen-containing compounds of copper, calculated as CuO, −0.1 to 3% by weight, in particular 1 to 3% by weight of oxygen-containing compounds of molybdenum, calculated as $MoO_3$, 0 to 5% by weight of further components, where the data in % by weight add up to 100% by weight and refer to the dry, nonreduced catalyst. According to the invention, particular preference is given to those catalysts which consist of the aforementioned components in the likewise aforementioned weight fractions.

One catalyst that is particularly preferred for use within the context of the process according to the invention consists to 49 to 53% by weight of NiO, to 15 to 19% by weight of CuO, to 28 to 32% by weight of $ZrO_2$ and to 1 to 2% by weight of $MoO_3$, and optionally to 0 to 3% by weight of further components, such as, for example, graphite, where the weight fractions selected in each case of the individual components are based on the dry, nonreduced catalyst and add up to 100% by weight. Catalysts of this type are known and can be prepared for example as described in EP 0 696 572.

The catalysts that can be used according to the invention can be prepared e.g. using precipitation methods. Thus, for example, they can be obtained through a joint precipitation of the nickel and copper components from an aqueous salt solution comprising these elements by means of mineral bases in the presence of a slurry of a sparingly soluble, oxygen-containing zirconium compound and subsequent washing, drying and calcination of the resulting precipitate. Sparingly soluble, oxygen-containing zirconium compounds which can be used are, for example, zirconium dioxide, zirconium oxide hydrate, zirconium phosphates, borates and silicates. The slurries of the sparingly soluble zirconium compounds can be prepared by suspending finely particulate powders of these compounds in water with vigorous stirring. These slurries are advantageously obtained by precipitating out the sparingly soluble zirconium compounds from aqueous zirconium salt solutions by means of mineral bases.

Preferably, the catalysts that can be used according to the invention are prepared via a joint precipitation (coprecipitation) of all of their components. For this, an aqueous salt solution comprising the catalyst components is expediently admixed, at elevated temperature and with stirring, with an aqueous mineral base, in particular an alkali metal base—for example sodium carbonate, sodium hydroxide, potassium carbonate or potassium hydroxide—until the precipitation is complete. The type of salts used is generally not critical—since what is primarily important in this procedure is the water solubility of the salts, a criterion is their good water solubility required for the preparation of these relatively highly concentrated salt solutions. It is considered self-evident that when selecting the salts of the individual components, only salts with those anions which do not lead to disturbances, whether by causing undesired precipitations or by hindering or preventing precipitation as a result of complex formation, are naturally chosen.

Catalysts with particularly advantageous properties that can be used according to the invention are obtainable by precipitating some of the zirconium component of the catalyst, expediently from an aqueous zirconium salt solution, separately in a precipitation apparatus by adding aqueous mineral bases. The remainder of the zirconium component of the catalyst can then be precipitated onto the preferably freshly precipitated zirconium oxide hydrate obtained in this way together with the other catalytically active components in a coprecipitation, as has been described above. In this connection, it has generally proven to be particularly expedient to preprecipitate 10 to 80% by weight, preferably 30 to 70% by weight and in particular 40 to 60% by weight of the total amount of zirconium in the catalytically active mass.

The catalysts prepared in this way can be stored and used as such. Prior to their use as catalysts in the course of the process according to the invention, they are usually prereduced. However, they can also be used without prereduction, in which case they are then reduced by the hydrogen present in the reactor under the conditions of the hydrogenation according to the invention. For the prereduction, the catalysts are generally firstly exposed to a nitrogen/hydrogen atmosphere at 150 to 200° C. over a period of from 12 to 20 hours and then further treated in a hydrogen atmosphere for up to ca. 24 hours at 200 to 300° C. During this prereduction, some of the oxygen-containing metal compounds present in the catalysts is usually reduced to the corresponding metals, meaning that these are present together with the various oxygen compounds in the active form of the catalyst.

In general, the catalysts according to the invention are preferably used in the form of unsupported catalysts. The term "unsupported catalyst" is used to refer to a catalyst which, in contrast to a supported catalyst, consists only of catalytically active mass. Unsupported catalysts can be used by introducing the catalytically active mass ground to powder into the reaction vessel or by arranging the catalytically active mass following grinding, mixing with molding auxiliaries, molding and heat-treating as catalyst moldings—for example as beads, cylinders, tablets, rings, spirals, strands and the like—in the reactor.

Within the context of a further embodiment of the hydrogenation process according to the invention, the selected heterogeneous catalyst is used in the form of a fixed-bed catalyst.

To carry out the process according to the invention, the compound of the formula (IV) described above is brought into contact with hydrogen and the selected catalyst. The hydrogen here can be used in undiluted form, usually in a purity of about 99.9% by volume, or in diluted form, i.e. in the form of mixtures with inert gases, such as, for example, nitrogen or argon. Preferably, hydrogen is used in undiluted form.

The reaction can take place with good success with or without the addition of a solvent. If the reaction takes place in the presence of a solvent, organic solvents that are inert under the reaction conditions are suitable, such as, for example, methanol, ethanol, isopropanol, hexane, heptane, cyclohexane and the like. Preferably, the reaction is carried out in methanol as solvent.

The hydrogenation according to the invention can be carried out at a hydrogen pressure (absolute) in the range from 1 to 200 bar, preferably from 2 or better from 3 to 200 bar, particularly preferably from 4 or 5 to 150 bar, particularly preferably from 5 to 100 bar and very particularly preferably in the range from 5 to 50 bar. The reaction temperature chosen here for carrying out the hydrogenation according to the invention is advantageously a temperature in the range from 20 to 150° C., preferably from 40 to 130° C., particularly preferably from 60 to 110° C. and very particularly preferably from 70 to 100° C.

In practice, the procedure during the implementation generally involves feeding the product of the formula (IV) to be reacted to the catalyst, which is usually located in a fixed-bed reactor preferably heated externally, such as, for example, a tubular reactor, autoclave or tube-bundle reactor, at the desired reaction temperature and the desired pressure. Here, the the catalyst is generally used at a rate of 0.1 to 1.0, preferably 0.1 to 0.6 and particularly preferably 0.2 to 0.4 kg of the compound of the formula (IV) per kg of catalyst and per hour. In this connection, it may be expedient to heat the product of the formula (IV) to be used prior to introduction into the reaction vessel or the reactor, preferably to the reaction temperature.

The hydrogenation process according to the invention can be carried out either discontinuously or continuously. In both cases, unreacted starting material can be circulated together with the hydrogen.

One preferred embodiment of the process according to the invention accordingly relates to a continuous process for the preparation of 2-substituted 4-hydroxy-4-methyltetrahydropyrans of the formula (I) comprising the steps a. providing a flow reactor comprising the selected strongly acidic cation exchanger;

b. continuously introducing isoprenol, the aldehyde of the formula (III) and water into the flow reactor;

c. continuously bringing isoprenol, the aldehyde of the formula (III) and water into contact with the strongly acidic cation exchanger in the flow reactor to give a reaction mixture comprising the desired compound of the formula (IV)

d. continuously hydrogenating the reaction mixture comprising the compound of the formula (IV), and e. continuously discharging the reaction mixture from the flow reactor.

The selected strongly acidic cation exchanger may be present here either in the form of a loose bed or in the form of a fixed bed in the aforementioned flow reactor.

It is also possible to carry out the reaction of isoprenol with the aldehyde of the formula (III) to be carried out according to the invention in a cascade of a plurality of, for example 2 or 3, successively connected flow reactors, where the individual flow reactors may also be filled with various strongly acidic cation exchangers and if using tubular reactors, these can be operated either in liquid phase mode or trickle mode. Moreover, the reaction mixture discharged from the selected flow reactor can, if desired, also be returned in part back to the continuously operated reaction.

The process according to the invention permits the preparation of 2-substituted 4-hydroxy-4-methyltetrahydropyrans of the formula (I), specifically the preparation of 2-isobutyl-4-hydroxy-4-methyltetrahydropyrans of the formula (I). These are usually produced in the form of reaction mixtures which, besides the desired target compounds, can also comprise radicals of the starting materials used, the water used and also possibly, to a slight extent, also the dehydrated by-products of the formulae (Va) and (Vb)

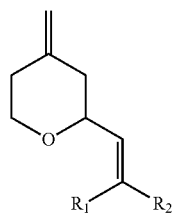

(Va)

(Vb)

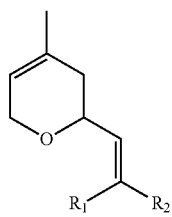

where R₁ and R₂ may have the meanings given under formula (I). The process according to the invention permits the preparation of the desired hydroxypyrans of the formula (I) or preferably of 2-isobutyl-4-hydroxy-4-methyltetrahydropyran in high yield and high purity, where the undesired dehydration products of the formulae (Va) to (Vb) are only produced to a minor extent, if at all.

Just like the unreacted starting compounds and/or the starting compounds used in excess, these by-products can be advantageously returned again to the reaction.

The reaction mixtures obtained according to the invention typically consist to an extent of about 50 to about 90% by weight, often to about 60 to about 80% by weight, of the desired 2-substituted 4-hydroxy-4-methyltetrahydropyrans of the formula (I) and only up to about 20% by weight, preferably only up to about 15% by weight and particularly preferably only up to 10% by weight, of the dehydration products of the formulae (IVa) to (IVc), in each case based on the total weight of the crude product obtained and moreover of the unreacted starting materials and/or starting materials used in excess, and the other specified by-products.

The substance mixtures obtained as crude product can be further purified easily by methods known to the person skilled in the art, in particular by distillation and/or rectification. In this way, the 2-substituted 4-hydroxy-4-methyltetrahydropyran of the formula (I) desired in each case, in particular when using isoprenol and prenal with subsequent hydrogenation, the desired 2-isobutyl-4-hydroxy-4-methyltetrahydropyran is obtained in a purity of more than 95% by weight or preferably from 97 to 99.9% by weight or particularly preferably from 98 to 99.8% by weight, i.e. in a quality as is required, for example, for use as aroma chemical.

One preferred embodiment of the process according to the invention relates to the preparation of 2-substituted 4-hydroxy-4-methyltetrahydropyrans in the form of mixtures of the cis-diastereomers of the formula (Ib)

(Ib)

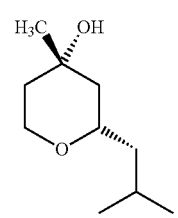

and of the trans-diastereomers of the formula (Ic)

(Ic)

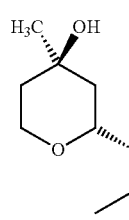

where the diastereomer ratio of the cis-diastereomer of the formula (Ib) to the trans-diastereomer of the formula (Ic) is 65:35 to 95:5, preferably 70:30 to 85:15.

In particular for the reaction of isoprenol with prenal with subsequent hydrogenation preferred according to the invention, in the course of the process according to the invention 2-isobutyl-4-hydroxy-4-methyltetrahydropyran is obtained in the form of mixtures of the cis-diastereomer of the formula (Ib)

(Ib)

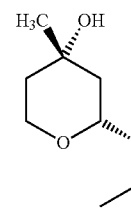

and of the trans-diastereomers (Ic)

(Ic)

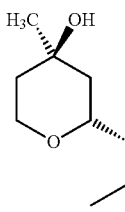

where the diastereomer ratio of the cis-diastereomer of the formula (Ib) to the trans-diastereomer of the formula (Ic) is 65:35 to 95:5, preferably 70:30 to 85:15. On account of their particular odor properties, mixtures of this type are suitable to a particular degree for use as aroma chemicals, for example as component with lily of the valley scent for producing fragrance compositions.

Within the context of one preferred embodiment, the present invention therefore provides a process for the preparation of 2-isobutyl-4-hydroxy-4-methyltetrahydropyran of the formula (Ia)

(Ia)

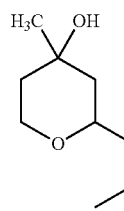

comprising the reaction of 3-methylbut-3-en-1-ol of the formula (II) with prenal of the formula (IIIa)

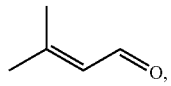
(IIIa)

in the presence of water and in the presence of a strongly acidic cation exchanger to form the product of the formula (IVa)

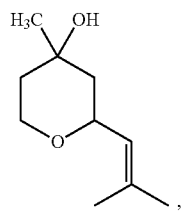
(IVa)

and subsequent catalytic hydrogenation in the presence of hydrogen and a nickel-containing catalyst to form the compound of the formula (Ia).

The examples below serve to illustrate the invention without limiting it in any way:

Gas chromatographic analyses were carried out in accordance with the following method: 30 m DB-WAX, ID.: 0.32 mm, FD.: 1.2 µm; 50° C., 3° C./min-170° C., 20° C./min to 240° C.; $t_R$=min; carrier gas: He; sample: 0.2 µl; $t_R$ (prenal): 9.1; $t_R$ (isoprenol): 10.6; $t_R$ (dehydrorose oxide of the formula (Va)): 15.6; $t_R$ (nerol oxide of the formula Vb)): 18.5; $t_R$ (trans-pyranol of the formula (Ic)): 28.5; $t_R$ (cis-pyranol of the formula (1b)): 29.8; $t_R$ (trans-hydroxyrose oxide of the formula Iva): 34.2; $t_R$ (cis-hydroxyrose oxide of the formula Iva): 35.4; $t_R$ (2-(2-hydroxymethylpropyl)-4-methyltetrahydropyranol): 41.5 and 42.2.

EXAMPLE 1

Preparation of Trans- and Cis-Hydroxyrose Oxide

Prior to use, the ion exchanger was firstly washed several times with water, then once with methanol and finally washed free of methanol with water.

1.7 g of Amberlyst™ 131 (58% by weight H₂O) and 4.2 g (0.05 mol) of isoprenol were introduced as initial charge in a flask at room temperature and then 4.3 g (0.05 mol) of prenal were added dropwise. The reaction mixture was stirred for 3 h at room temperature. The fully reacted reaction mixture was admixed with 30 ml of MTBE and the ion exchanger was then filtered off. The ion exchanger was washed twice with in each case 5 ml of MTBE. The resulting reaction solution was analyzed by gas chromatography (in GC area %). The yellow filtrate was concentrated on a rotary evaporator, giving 7.1 g of crude product.

| prenal | 1.8 GC area % |
|---|---|
| isoprenol | 3.8 GC area % |
| dehydrorose oxide | 1.6 GC area % |
| nerol oxide | 4.5 GC area % |
| trans-hydroxyrose oxide | 17.7 GC area % |
| cis-hydroxyrose oxide | 67.5 GC area % |

EXAMPLE 2

Preparation of Trans- and Cis-Hydroxyrose Oxide 1.7 g (20% by weight) of Amberlyst™ 131 (58% by weight H₂O) and 4.2 g (0.05 mol) of isoprenol were introduced as initial charge in a flask at room temperature and then 4.3 g (0.05 mol) of prenal were added dropwise. The reaction mixture was stirred for 1 h at 60° C. After cooling the fully reacted reaction mixture MTBE (30 ml) was added and the ion exchanger was then filtered off. The ion exchanger was washed twice with in each case 5 ml of MTBE. The resulting reaction solution was analyzed by gas chromatography (in GC area %). The yellow filtrate was concentrated on a rotary evaporator, giving 7.6 g of crude product.

| prenal | 0.9 GC area % |
|---|---|
| isoprenol | 1.2 GC area % |
| dehydrorose oxide | 1.8 GC area % |
| nerol oxide | 4.5 GC area % |
| trans-hydroxyrose oxide | 31.1 GC area % |
| cis-hydroxyrose oxide | 55.5 GC area % |
| 2-(2-hydroxymethylpropyl)-4-methyltetrahydropyranol | 2.7 GC area % |

EXAMPLE 3

Preparation of Trans- and Cis-Hydroxyrose Oxide 1.7 g (20% by weight) of Amberlyst™ 131 (58% by weight H₂O) and 4.2 g (0.05 mol) of isoprenol were introduced as initial charge in a flask at room temperature and then 4.3 g (0.05 mol) of prenal were added dropwise. The reaction mixture was stirred for 1 h at 80° C. After cooling the fully reacted reaction mixture, MTBE (30 ml) was added and the ion exchanger was then filtered off. The ion exchanger was washed twice with in each case 5 ml of MTBE. The resulting reaction solution was analyzed by gas chromatography (GC area %). The yellow filtrate was concentrated on a rotary evaporator, giving 7.6 g of crude product.

| prenal | 0.4 GC area % |
|---|---|
| isoprenol | 0.3 GC area % |
| dehydrorose oxide | 1.7 GC area % |
| nerol oxide | 4.9 GC area % |
| trans-hydroxyrose oxide | 46.1 GC area % |
| cis-hydroxyrose oxide | 27.3 GC area % |
| 2-(2-hydroxymethylpropyl)-4-methyltetrahydropyranol | 13.5 GC area % |

EXAMPLE 4

Preparation of Trans- and Cis-Pyranol

In a 300 ml laboratory autoclave, 20 g of hydroxyrose oxide dissolved in 80 ml of methanol were hydrogenated in the presence of 20 g of a catalyst consisting of 50% by weight of NiO, 17% by weight of CuO, 30.5% by weight of ZrO₂ and 1.5% by weight of MoO₃ in the form of tablets with a diameter and a height of in each case 3 mm at a hydrogen pressure of 30 bar and a temperature of 95° C. with vigorous stirring.

After a reaction time of 4 h, the catalyst was filtered off. The resulting reaction mixture was analyzed by gas chromatography at the times given in Table 1. This gave the results given in Table 1 (in each case in GC area %, conversion: 99% and selectivity: 95%).

TABLE 1

| Time (h) | 0 | 2 | 4 |
|---|---|---|---|
| trans-hydroxyrose oxide | 55.5 | 4.5 | 0.4 |
| cis-hydroxyrose oxide | 36.4 | 2.9 | 0.3 |
| trans-pyranol | 0 | 55.4 | 57.6 |
| cis-pyranol | 0 | 34.0 | 36.3 |

The invention claimed is:

1. A process for the preparation of 2-substituted 4-hydroxy-4-methyltetrahydropyrans of the formula (I)

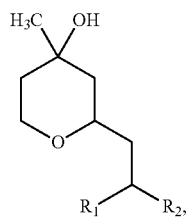

(I)

where the radical $R_1$ is a straight-chain or branched alkyl radical having 1 to 5 carbon atoms, and $R_2$ is hydrogen or a straight-chain or branched alkyl radical having 1 to 3 carbon atoms, which comprises reacting 3-methylbut-3-en-1-ol of the formula (II)

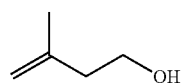

(II)

with an aldehyde of the formula (III)

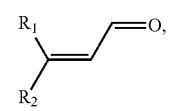

(III)

wherein the radicals $R_1$ and $R_2$ have the same meanings as given in formula (I), in the presence of water and in the presence of a strongly acidic cation exchanger to form the compound of the formula (IV)

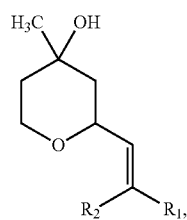

(IV)

and hydrogenation of the compound of the formula (IV) to give a compound of the formula (I), wherein the hydrogenation is carried out in the presence of hydrogen and a catalyst comprising
30 to 70% by weight of oxygen-containing compounds of nickel, calculated as NiO,
15 to 45% by weight of oxygen-containing compounds of zirconium, calculated as $ZrO_2$,
5 to 30% by weight of oxygen-containing compounds of copper, calculated as CuO and
0.1 to 10% by weight of oxygen-containing compounds of molybdenum, calculated as $MoO_3$, optionally
0 to 10% by weight of further components,
where the data in % by weight refer to the dry, nonreduced catalyst.

2. The process according to claim 1, wherein the radical $R_1$ is a straight-chain or branched alkyl radical having 1 to 3 carbon atoms.

3. The process according to claim 1, wherein the radical $R_2$ is methyl or ethyl.

4. The process according to claim 1, wherein 3-methylbut-3-en-1-ol of the formula (II) and the aldehyde of the formula (III) are used in a molar ratio of from 0.7:1 to 2:1.

5. The process according to claim 1, wherein $R_1$ and $R_2$ are methyl and wherein 3 methylbut-3-en-1-ol of the formula (II) and the aldehyde of the formula (III) are used in a molar ratio of from 1:1 to 1.5:1.

6. The process according to claim 1, wherein the reaction of 3 methylbut-3-en-1-ol of the formula (II) with an aldehyde of the formula (III) is carried out without addition of an organic solvent.

7. The process according to claim 1, wherein the reaction of 3 methylbut-3-en-1-ol of the formula (II) with an aldehyde of the formula (III) is carried out at a temperature in the range from 20 to 80° C.

8. The process according to claim 1, wherein the reaction of 3 methylbut-3-en-1-ol of the formula (II) with an aldehyde of the formula (III) is carried out continuously.

9. The process according to claim 1, wherein the reaction of 3 methylbut-3-en-1-ol of the formula (II) with the aldehyde of the formula (III) is carried out in the presence of methanol.

10. The process according to claim 1, wherein the catalyst is used in the form of an unsupported catalyst.

11. The process according to claim 1, wherein the catalyst is used in the form of a fixed-bed catalyst.

12. The process according to claim 1, wherein the hydrogenation is carried out at a temperature in the range from 50 to 130° C.

13. The process according to claim 1, wherein the hydrogenation is carried out at a hydrogen pressure in the range from 5 to 200 bar absolute.

14. The process according to claim 1, wherein the hydrogenation is carried out continuously.

15. The process according to claim 1, wherein the reaction of 3 methylbut-3-en-1-ol of the formula (II) with the aldehyde of the formula (III) is carried out in the presence of an organic solvent.

16. The process according to claim 1, comprising the steps
a. providing a flow reactor comprising the strongly acidic cation exchanger;
b. continuously introducing 3 methylbut-3-en-1-ol of the formula (II), the aldehyde of the formula (III) and water into the flow reactor;
c. continuously bringing 3 methylbut-3-en-1-ol of the formula (II), the aldehyde of the formula (III) and water into contact with the strongly acidic cation exchanger in the flow reactor to give a reaction mixture comprising the compound of formula (IV),
d. continuously hydrogenating the reaction mixture comprising the compound of the formula (IV), and
e. continuously discharging the reaction mixture from the flow reactor.

17. The process according to claim 1 for the preparation of 2-substituted 4-hydroxy-4-methyltetrahydropyrans of the formula (I) in the form of mixtures of the cis-diastereomer of the formula (Ib)

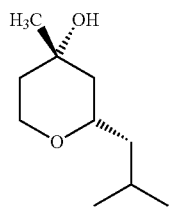

(Ib)

and of the trans-diastereomer of the formula (Ic)

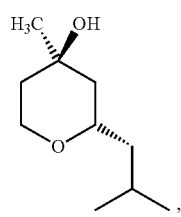

(Ic)

wherein the diastereomer ratio of the cis-diastereomer of the formula (Ib) to the trans-diastereomer of the formula (Ic) is 65:35 to 95:5.

18. The process according to claim 9, wherein the catalyst comprises:
40 to 60% by weight of oxygen-containing compounds of nickel, calculated as NiO,
20 to 40% by weight of oxygen-containing compounds of zirconium, calculated as $ZrO_2$,
10 to 25% by weight of oxygen-containing compounds of copper, calculated as CuO and
0.5 to 5% by weight of oxygen-containing compounds of molybdenum, calculated as $MoO_3$, and optionally
0 to 5% by weight of further components.

* * * * *